United States Patent
Ranjan et al.

(10) Patent No.: US 12,105,039 B2
(45) Date of Patent: Oct. 1, 2024

(54) SYSTEMS AND METHODS FOR IN-SITU MEASUREMENT OF SHEET RESISTANCE ON SUBSTRATES

(71) Applicant: Lam Research Corporation, Fremont, CA (US)

(72) Inventors: Manish Ranjan, Sherwood, OR (US); Andrew James Pfau, Portland, OR (US); Douglas Hill, Tigard, OR (US); Douglas Koeller, Beaverton, OR (US); Burton Williams, Portland, OR (US); Shantinath Ghongadi, Tigard, OR (US)

(73) Assignee: Lam Research Corporation, Fremont, CA (US)

( * ) Notice: Subject to any disclaimer, the term of this patent is extended or adjusted under 35 U.S.C. 154(b) by 157 days.

(21) Appl. No.: 17/765,407

(22) PCT Filed: Sep. 29, 2020

(86) PCT No.: PCT/US2020/053316
§ 371 (c)(1),
(2) Date: Mar. 30, 2022

(87) PCT Pub. No.: WO2021/076321
PCT Pub. Date: Apr. 22, 2021

(65) Prior Publication Data
US 2022/0349850 A1 Nov. 3, 2022

Related U.S. Application Data
(60) Provisional application No. 62/916,719, filed on Oct. 17, 2019.

(51) Int. Cl.
| | | |
|---|---|---|
| *G01N 27/04* | (2006.01) | |
| *C23C 14/52* | (2006.01) | |
| *G01N 33/20* | (2019.01) | |

(52) U.S. Cl.
CPC .......... *G01N 27/041* (2013.01); *C23C 14/52* (2013.01); *G01N 33/20* (2013.01)

(58) Field of Classification Search
CPC ....... C23C 14/52; G01N 27/041; G01N 33/20
See application file for complete search history.

(56) References Cited

U.S. PATENT DOCUMENTS

| | | | |
|---|---|---|---|
| 5,698,989 A | 12/1997 | Nulman | |
| 7,999,540 B2* | 8/2011 | Miller | ............... H01L 21/67253 324/239 |

(Continued)

FOREIGN PATENT DOCUMENTS

| | | |
|---|---|---|
| CN | 102297893 A | 12/2011 |
| CN | 114556096 | 5/2022 |

(Continued)

OTHER PUBLICATIONS

International Application Serial No. PCT/US2020/053316, International Search Report mailed Jan. 13, 2021, 3 pgs.

(Continued)

*Primary Examiner* — Jay Patidar
(74) *Attorney, Agent, or Firm* — Schwegman Lundberg & Woessner, P.A.

(57) ABSTRACT

In some examples, a Vacuum Pre-treatment Module (VPM) metrology system is provided for measuring a sheet resistance of a layer on a substrate. The system may comprise an eddy sensor including a sender sensor and a receiver sensor defining a gap between them for accepting an edge of a substrate to be tested. A sensor controller receives measurement signals from the eddy sensor. A data processor processes the measurement signals and generates sheet resistance values for the layer on the substrate.

19 Claims, 7 Drawing Sheets

(56) References Cited

U.S. PATENT DOCUMENTS

| | | | |
|---|---|---|---|
| 9,153,482 B2 | 10/2015 | Knisley et al. | |
| 2008/0186022 A1* | 8/2008 | Lei | G01B 7/105 |
| | | | 324/230 |
| 2014/0002062 A1* | 1/2014 | Lu | G01B 7/105 |
| | | | 324/207.13 |
| 2018/0164251 A1 | 6/2018 | Hand et al. | |
| 2021/0102982 A1* | 4/2021 | Morimitsu | C23C 14/52 |
| 2023/0228713 A1* | 7/2023 | Matsui | G01N 27/80 |
| | | | 324/243 |

FOREIGN PATENT DOCUMENTS

| | | |
|---|---|---|
| JP | H05149927 A | 6/1993 |
| JP | 2002141339 A | 5/2002 |
| JP | 2022551897 | 12/2022 |
| KR | 19990041116 A | 6/1999 |
| KR | 20110011297 A | 2/2011 |
| WO | WO-2019187393 A1 | 10/2019 |

OTHER PUBLICATIONS

International Application Serial No. PCT/US2020/053316, Written Opinion mailed Jan. 13, 2021, 5 pgs.
"International Application Serial No. PCT US2020 053316, International Preliminary Report on Patentability mailed Apr. 28, 2022", 7 pgs.
Taiwanese Application Serial No. 109135311, Office Action mailed Jul. 2, 2024, with English Translation, 46 pgs.

* cited by examiner

SYSTEMS AND METHODS FOR IN-SITU MEASUREMENT OF SHEET RESISTANCE ON SUBSTRATES

CLAIM OF PRIORITY

This application is a U.S. National Stage Filing under 35 U.S.C. 371 from International Application No. PCT/US2020/053316, filed on Sep. 29, 2020, and published as WO 2021/076321 A1 on Apr. 22, 2021, which claims the benefit of priority to Ranjan et al, U.S. Provisional Application No. 62/916,719, filed Oct. 17, 2019, entitled "EDDY BASED IN-SITU MONITORING OF SURFACE OXIDE ON SUBSTRATES POST METALLIZATION," each of which is incorporated herein by reference in its entirety.

FIELD

The present disclosure relates generally to methods and apparatus for metrology in a Vacuum Pretreatment Module (VPM) and, in one example, to in-situ oxide metrology techniques in substrate processing.

BACKGROUND

Copper or cobalt electroplating typically includes deposition on a substrate, such as a substrate, of a thin metal seed layer. The deposition may occur, for example, by physical vapor deposition or by chemical vapor deposition (CVD) to form a conductive substrate prior to electroplating. After a seed layer deposition in a vacuum chamber, the substrate is removed from the vacuum chamber and exposed to clean room ambient air. In some instances, there is a wait time ranging from a few minutes to several days before the substrate is electroplated.

The wait time (or seed aging) can cause oxidation of the seed layer and change the surface wetting characteristics. This oxidation may result in defects on the substrate. Post electroplating voids and pits have been observed, particularly on pattern substrates. This potentially renders useless any device made from the defective substrate. Overall production yields can thus be negatively impacted by seed layer aging.

The negative effects of seed aging and oxidation may multiply as seed layer thicknesses are reduced, for example, to enable nanosized structures of high technology nodes. Seed dissolution and a reduction in current density may also be seen in localized spots in thinner seed layers. The localized spots can reach deeper into vias and trenches, particularly on substrates that have a relatively high pattern density. This can exacerbate post-electroplating defects on substrates.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In some examples, a Vacuum Pre-treatment Module (VPM) metrology system is provided for measuring a sheet resistance of a layer on a substrate. The system may comprise an eddy sensor, the eddy sensor including a sender sensor and a receiver sensor defining a gap between them for accepting an edge of a substrate to be tested; a sensor controller to receive measurement signals from the eddy sensor; and a data processor to process the measurement signals and generate sheet resistance values for the layer on the substrate.

In some examples, the system further comprises a trigger sensor to detect a threshold proximity of the substrate and generate a signal to initiate activation of the sender and receiver sensors.

In some examples, a size of the gap is in the range 3-50 mm. In some examples, wherein the gap size is 5 mm.

In some examples, the eddy sensor is configured to take a measurement at a measurement position on the substrate, wherein the measurement position is disposed at a location midway between a center of the substrate and an edge of the substrate.

In some examples, the system is configured to measure sheet resistance for a copper (Cu) seed substrate in the range of approximately 0.001 to 30 ohms-per-square (ohm/sq).

In some examples, the system is configured to measure sheet resistance for a cobalt (Co) seed substrate in the range of approximately 1 ohm/sq to 10,000 ohm/sq.

In some examples, the system is configured to measure sheet resistance up to 50,000 ohm/sq.

In some examples, the eddy sensor is disposed immediately adjacent an outbound load lock (OBLL) of the VPM and is configured to accept substrates in-situ for sheet resistance measurements during a production run of the VPM.

In some examples, a straight-line path of a substrate exiting the OBLL for a sheet resistance measurement is coincident with an in-line scan path of the eddy sensor.

BRIEF DESCRIPTION OF THE DRAWINGS

Some embodiments are illustrated by way of example and not limitation in the views of the accompanying drawing.

DESCRIPTION

The description that follows includes systems, methods, techniques, instruction sequences, and computing machine program products that embody illustrative embodiments of the present disclosure. In the following description, for purposes of explanation, numerous specific details are set forth in order to provide a thorough understanding of example embodiments. It will be evident, however, to one skilled in the art that the present disclosure may be practiced without these specific details.

A portion of the disclosure of this patent document may contain material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to any data as described below and in the drawings that form a part of this document: Copyright Lam Research Corporation, 2019, All Rights Reserved.

As discussed above, copper or cobalt electroplating typically includes deposition on a substrate of a thin metal seed layer. The deposition may occur, for example, by physical vapor deposition or by CVD to form a conductive substrate prior to electroplating. After the seed layer deposition in a vacuum chamber, the substrate is removed from the vacuum chamber and exposed to clean room ambient air. In some instances, there is a wait time ranging from a few minutes to several days before the substrate is electroplated.

The wait or delay time (or so-called seed aging) can cause oxidation of the seed layer and change the surface wetting characteristics. This oxidation may result in defects on the substrate. Post electroplating voids and pits have been observed, particularly on pattern substrates. This renders any device made from the defective substrate essentially useless. Overall yield can thus be negatively impacted by seed layer aging.

The negative effects of seed aging and oxidation may even increase as seed layer thicknesses are reduced (for example, to enable nano-sized structures of high technology nodes). Seed dissolution and a reduction in current density may also be seen in localized spots in thinner seed layers. The localized spots can reach deeper into the vias and trenches, particularly on substrates that have a relatively high pattern density. This can exacerbate post-electroplating defects on substrates.

In some examples, a VPM is used to pretreat substrates using hydrogen ($H_2$) plasma to reduce oxide growth on a substrate surface. While a VPM can be effective in reducing the impact of seed aging, the ability to qualify or quantify VPM performance in the field (and in-line in operation) has proven very challenging. For example, in previous attempts to qualify the performance of a VPM, one or more substrates are oxidized in a controlled environment for comparison against identical substrates pretreated by a VPM. Pre-treatment and post-treatment sheet resistance measurements are performed, and a measured (or calculated) sheet resistance drop is used to characterize the performance of the VPM. Even though this technique may be useful in identifying oxidation changes on the substrate pre and post VPM treatment, this technique is still plagued with several problems in the field.

For instance, since the sheet resistance measurement is performed offline, there is a variable wait time (or queue time) after the substrate is treated in the VPM during which the treated substrate can still oxidize. This variable element can undermine the performance measurement of the VPM. In fact, if the queue time post VPM is sufficiently long, a substrate can regrow almost all the oxide back before sheet resistance measurement can be taken. Offline techniques are therefore not suitable to qualify a VPM in the field as the queue time cannot be tightly controlled. The present disclosure thus seeks to provide in-situ measurement techniques for inline (in field) sheet resistance measurement during real-time VPM operations, and to characterize the performance of the VPM accordingly.

Figure 1:
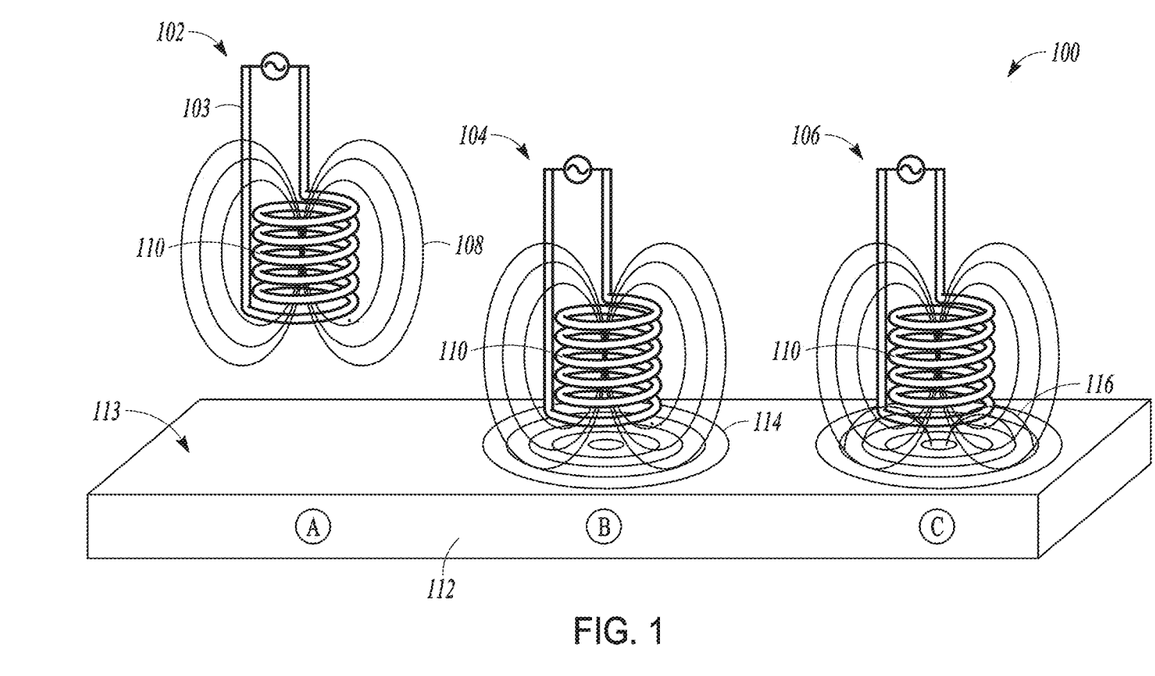
FIG. 1 is a schematic diagram, for purposes of explanation, of an array of coils, according to some example embodiments.

With reference to FIG. 1, an array 100 of coils 110 is shown. At position 102, an alternating current (AC) flowing through the coil 110 of a probe (or sensor) 103 at a chosen frequency generates a magnetic field 108 around the coil. At position 104, when the coil 110 is placed close to an electrically conductive material or substrate 112, an eddy current 114 is induced in the material 12. In some examples, at position 106, if a flaw (e.g., an oxidation in a layer such as a seed layer 113 on the substrate 112) in the conductive material disturbs the eddy current circulation, the magnetic coupling with the probe 103 is changed and a defect signal 116 can be read by measuring the coil impedance variation. In some examples, this method is used to determine how much conductive material is present (i.e. thickness of non-oxidized seed), as opposed to determining defects in the film continuity. The comparison is made to compare wafers with same amounts of seed deposition, but differing levels of oxidation, wherein the more oxidized seed is less conductive and thus carries less of an eddy current. The characteristics of the eddy currents 114 may be determined or affected by the 112 material characteristics. The eddy currents 114 can generate a secondary magnetic field opposed to the primary field. The impedance of the coil 110 may be affected by material 112 differences that can influence an eddy current signal.

Figure 2:
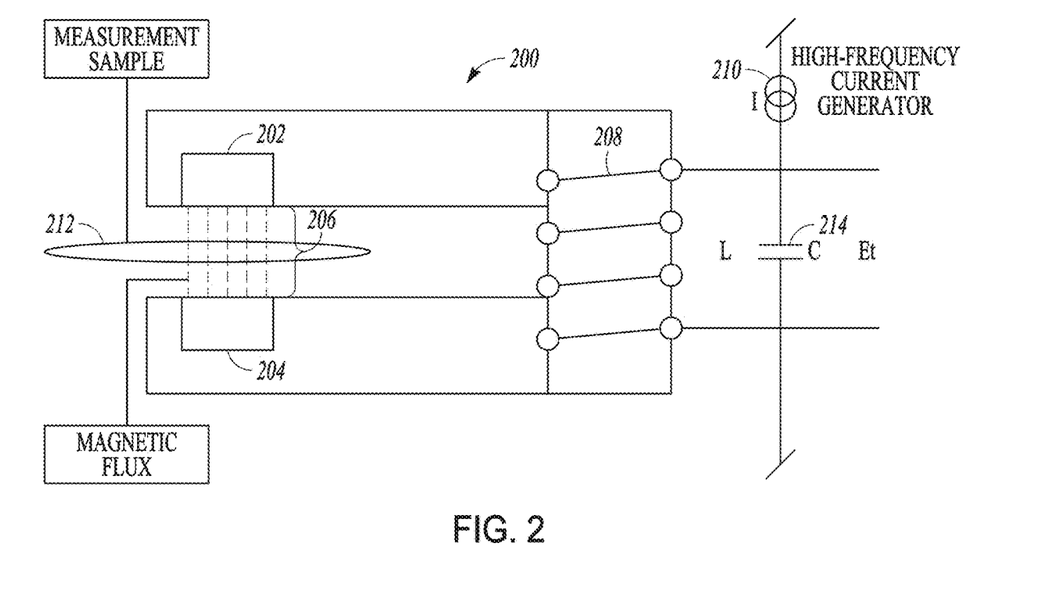
FIG. 2 is a schematic view of an eddy sensor and related aspects, according to an example embodiment.

With reference to FIG. 2, in some examples, an eddy sensor 200 comprises a pair of magnetic coupling sensors respectively referred to as a sender (or first sensor 202 and a receiver (or second) sensor 204. In some examples, the sender or first sensor 202 and the receiver or second sensor 204 are analogous to the probe 103 of FIG. 1 and operate in a similar way. A gap 206 exists between the sender 202 and receiver 204 sensors. The eddy sensor 200 includes a coil 208 through which an AC can flow at a certain frequency. The AC and frequency may be generated by a generator 210. The AC flow through the coil 208 generates a time varying magnetic field. A measurement sample 212 (such as a metal substrate, or a seed layer) passing through the sender 202 and receiver 204 sensors generates a surface eddy current, which in turn generates its own magnetic field which is opposed to the original magnetic field generated by the coil 208. The net change in the magnetic field changes the impedance (L) of a receiver circuit 214. The impedance change is sensed by a sensor controller, discussed further below with reference to FIG. 3, for example. The change in impedance (L) is proportional to the strength of the eddy sensor signal generated by the substrate 212 (e.g. seed layer) which in turn is related to the sheet resistance of the substrate 212.

Figure 3:
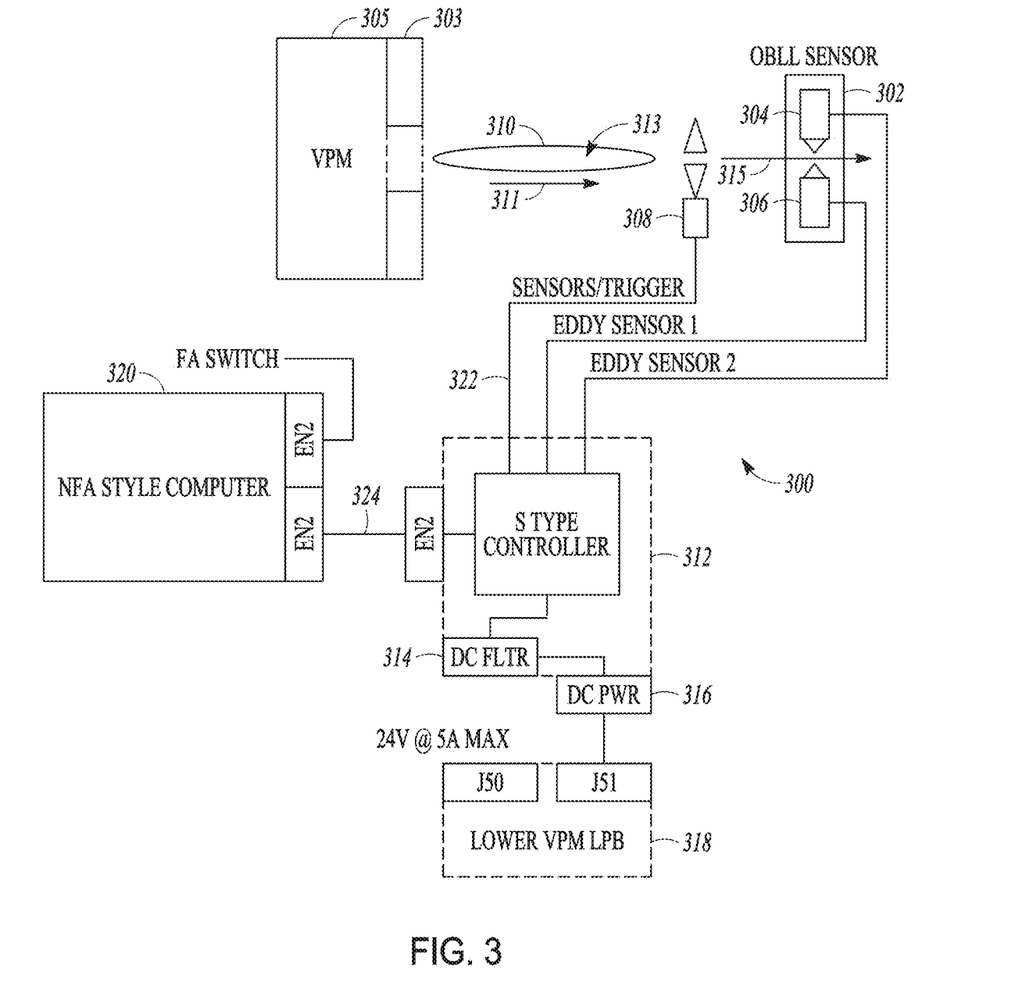
FIG. 3 is a schematic view of aspects of a VPM metrology system, according to an example embodiment.

FIG. 3 illustrates example aspects of a Vacuum Pre-Treatment Module (VPM) metrology system 300, as termed herein. The system 300 includes an eddy sensor 302 arranged next to an outbound load lock (OBLL) 303 of a VPM 305. A load lock 303 allows entry and egress of elements into or out of a VPM 305 without breaking the vacuum therein. As above, the example eddy sensor 302 includes a pair of sensors, a sender receiver 304, and a receiver sensor 306. A trigger sensor 308 detects the approach of a substrate (for example, a wafer 310). A triggering of the trigger sensor 308 by an approaching wafer 310 (for example, exiting e the OBLL 303) activates (i.e., initiates an activation of) the sender 304 and receiver 306 sensors so that this pair of sensors do not have to remain activated continuously. They are only activated when necessary.

In some examples, a pair of eddy sensors 304 and 306 is installed outside an OBLL with a 5 mm gap between the sensors to measure sheet resistance in a "line-scan" on the substrate 310 post treatment in a VPM. Example sensor support components may include bracket parts that include sensor mounting slots extending in a vertical direction to adjust the gap between the sensors 304 and 306. An example gap size may be in the range 3-50 mm. In some examples, a suitable gap between the sensors is approximately 5 mm. Smaller gaps may reduce eddy current spot size (see below) and improve the accuracy of the sheet resistance measurement.

Example bracket parts may also include one or more sensor mounting slots extending in the horizontal direction to slide the sensors to a location (such as a measurement position) on the substrate to be measured. In some examples, measurements are not taken at a substrate edge nor proximate a substrate center. At the substrate edge, part of the eddy current is outside the substrate. At the substrate center, the eddy current can be influenced by a metal end effector (see below) and impact the accuracy of the measurement. In some examples, a measurement position is located approximately mid substrate (for example, approximately 75 mm from a substrate edge on 300 mm substrate or 50 mm from substrate edge on 200 mm substrate, and so on). In another embodiment, the measurement position can be closer to the edge, for example in a range approximately 5 mm from the substrate edge to approximately 5 mm away from the center of the substrate. In this embodiment, correction factors can be used to account for its proximity to the substrate edge and to the substrate center closer to the end effector. In this specification, the term "approximately" in relation to a given value means the value, plus or minus 10%.

Measurement and other signals from the sender 304, receiver 306, and trigger 308 sensors are transmitted to a sensor controller 312. The sensor controller 312 may include one or more filters 314, and direct current (DC) processing elements 316. The sensor controller 312 is powered by a power source 318. Measurement and automation software (described in more detail below) is processed by a system computer 320. Respective circuitry 322 and 324 interconnect the sensors 304, 306, 308, the sensor controller 312, and the system computer 320.

In some examples, a measured sheet resistance for a copper (Cu) seed substrate 310 is in the range of approximately 0.001 to 30 ohms-per-square (ohm/sq). In some examples, a measured range of sheet resistance of a cobalt (Co) or alloy seed substrate is in the range of approximately 1 ohm/sq to 50,000 ohm/sq. In some examples, a VPM metrology system (for example VPM metrology system 300, FIG. 3) enables sheet resistance measurements in the range of approximately 1 m ohm/sq to 10.000 ohm/sq depending on a calibration range, as discussed further below. Various calibration and system setup steps and configurations can be used to extend the range of the sheet resistance up to 50,000 ohm/sq if desired.

A typical change in sheet resistance in a seed layer before and after pre-treatment in a VPM can range from approximately 5 to 25%. Lower noise and signal stability are sometimes important for accurately measuring a small change in the sheet resistance value on the same substrate when measured before and after the VPM pre-treatment. Some examples, therefore, include tightly controlled hardware and system configurations to help achieve an acceptable signal-to-noise ratio in sheet resistance measurements.

Some examples of a VPM metrology system include a hardware package and a measurement technique configured to provide inline measurement of an oxidized or reduced seed-layer substrate (or seed substrate) (i.e., while operating a VPM in production). The inline measurement qualifies a VPM and provides an assessment of its performance. In one example, a VPM hardware assembly includes configured mounting hardware, a set of eddy sensors, one or more sensor controllers, and one or more data processors configured to provide a large range of high signal-to-noise sheet (i.e., seed layer) resistance measurements. The measurements may be used for optimization of processes in electroplating tools, for example. An example VPM metrology system may include one set of eddy sensors for post VPM measurement or two sets of eddy sensors for both pre and post measurement in the associated substrate-processing tool. An example VPM metrology system can be integrated with the tool to provide real time sheet resistance measurements and the data can be used to prevent unintended VPM-related performance excursion and substrate scraps.

In some examples, as part of a hardware setup phase, both sensor gap and the sensor alignment are carefully configured to generate an acceptable signal stability and low noise ratio so that the desired range of sheet resistance can be measured with a desired accuracy. For example, the size of a measurement spot (i.e., a wafer location at which the sender and receiver sensors take a measurement) can be established in proportion to the gap distance. For example, a spot size may be set at approximately ~1.5 to 4 times a sensor gap distance depending on the range of sheet resistance being measured. A smaller sensor gap may increase the resolution of the data when sensor measurements are taken at multiple different locations on the wafer.

With regard to hardware placement and installation, some example VPM metrology systems 300 are configured to minimally impact the workflow through a tool to which the VPM metrology system is fitted. In some examples, a VPM metrology system is configured to take a measurement on a moving substrate when the substrate comes out of the tool through an OBLL. The sender and receiver sensor installation locations may be configured to reside closely proximate the OBLL door such that measurement queue time post VPM treatment is minimized.

In some examples, a wafer sheet resistance measurement is initiated or completed by a VPM metrology system 300 based on a combination of events (for example, an event of the OBLL opening and/or another event of a robot picking the wafer out of the OBLL). In some examples, the robot is a back-end robot that can pick the wafer up and move it out of the OBLL in a straight-line path 311 (FIG. 3). This straight-line path 311 enables a sheet resistance measurement to be performed for a wafer 310 (or a seed layer 313 on the wafer 310) as a linear line-scan 315 on the wafer. In another embodiment, the path of the back-end robot can be tuned to move in an arc shape on the wafer for continuous measurements. In yet another embodiment, a set of locations of the wafer can be selected and back end robot can be programmed to move to the selected locations on the wafer for continuous or scattered point data collection.

A frequency of substrate measurement may be established to allow multiple substrate measurements for obtaining information on "within substrate" uniformity in the line-scan direction. In some examples, an optimal substrate travel speed is determined to yield both an accurate measurement and also minimize tool throughput impact. For example, some impact on accuracy was seen with a substrate speed in the line-scan direction above 0.5 m/s. In some examples, an optimal substrate speed is below approximately 0.2 m/s for acceptably accurate and stable measurements. In some embodiments, >0.5 m/s line scan speed can be used with high throughput applications with correction factor for accurate measurements.

As mentioned above, a relatively small gap between the sensors (for example sender 304 and receiver 306, FIG. 3) may help to reduce the measurement position size. This size reduction may in turn increase measurement resolution and assist in measuring "within substrate" uniformity in sheet resistance. However, in some instances, reducing the gap has other less helpful side effects such as reducing signal stability, increasing signal sensitivity to tolerances in the hardware setup, causing or exacerbating tool/substrate vibration, and/or introducing drift into the system measurements. Efforts to implement a smaller gap can also be limited by substrate/tool vibration caused by substrate movement through the sensors (sender and receiver). On the other hand, the sensor gap should be large enough to allow thicker substrates to pass through the gap and should not impart vibration to the substrate during movement through the sensors. In some examples, a suitable gap between the sensors (sender and receiver) is in the range of approximately 3 to 50 mm. In some examples, the relatively lower end of this gap range is more suitable for Co seed layer applications, while a larger gap may be more suitable for Cu seed layer measurement in which sheet resistance is typically lower. In some examples, better noise characteristics are seen with lower sheet resistance measurements in which, for example, a sheet resistance of less than 10 ohm/sq range exhibits relatively lower noise and acceptable measurement attributes.

In some examples, testing was performed to determine a hardware sensitivity of a VPM metrology system 300. Some edge effects were seen when measurements were taken at the substrate edge and part of the eddy perturbed by the edge of the substrate. Typical edge effects revealed that signal noise and edge effects increase with a larger sensor gap. Thus, in some examples, an edge compensation is included in system calibration to enable sheet resistance measurements to be taken closer to a substrate (seed layer) edge.

In some examples, some interaction of the eddy sensors (sender and receiver) was seen with the robot (discussed further above), in particular with an end effector of the robot. The end effector is a metallic element and it can interfere with the sensor eddy current if a sheet resistance measurement is taken relatively close to the end effector. Metal end effectors are needed in the tool for stable substrate transfer and reliability. In some examples, a robot end effector holds the substrate by vacuum applied underneath the substrate (on the "silicon (Si) side") at the center of the substrate. In some examples, the substrate line-scan measurement location is chosen such that it is disposed away from the substrate edge to minimize edge effects and also away from metallic end effector to minimize interference with eddy current signals. In some examples, a measurement line-scan location is disposed approximately midway between an edge and a center of the substrate to be tested and parallel to the horizontal axis of the end effector.

In some examples, a vertical placement (height above a datum) of the sender and receiver sensors (for example, sensors 304 and 306, FIG. 3) is set such that the gap between the sensors is aligned with the opening in an OBLL door. This vertical placement (i.e., the sensor gap and OBLL door being placed substantially in the same horizontal plane) facilitates the taking of a line-scan measurement at the targeted location. An axial alignment between the two sensors is optimized to seek to ensure that the magnetic field lines are uniform through the distribution. Disturbances in the magnetic field have been seen to increase and introduce noise when the sender and receiver sensor alignment is out of spec. Optimal setup includes aligned sensors with <0.5 mm offset; however, a larger offset [<5 mm] could also work with lower sheet resistance measurements and better calibration.

In some examples, accurate eddy sensor calibration is important for measurement accuracy. In some examples, conventional 4-point (4-pt) probe methods and sheet resistance measurements were used as a calibration benchmark for the eddy-based methods. Conventionally, a 4-pt probe is used as an industry standard for sheet resistance measurements. In this regard, a set of calibration sheets with known sheet resistance may be used for eddy sensor calibration. However, a range of issues may present themselves when using conventional calibration sheets. Some present examples address these challenges by using a configured set of stable calibration substrates. As one such issue, a calibration sheet may have a higher sheet resistance variability across the sheet depending on the sheet deposition process. A calibration sheet may have repeatability issues. This variability is difficult to factor out of conventional calibration techniques. Moreover, as noted above, typical metallic deposited substrates tend to oxidize when exposed to ambient air. The native oxidation process can keep going for several weeks to months and the sheet resistance of calibration substrates will continue to change. Stable sheet resistance can therefore be a significant attribute for accurate and repeatable calibration across the sensors and for sensor-to-sensor matching.

Another challenge in calibration may arise in that an eddy sensor takes measurement through a single substrate. If there are multiple stacks on a seed layer substrate, the eddy sensor will detect a net sheet resistance and not necessarily a sheet resistance of an individual seed layer. By contrast, 4-pt probe methods typically measure the sheet resistance of the top film only. Substrate deposition processes are typically based on silicon substrate and most of the silicon used in the semiconductor industry is p or n doped in a silicon substrate which has some conductivity. When a metal film, such as a seed layer, is deposited on top of the conductive silicon substrate, the net sheet resistance measured by an eddy sensor factors in, or accounts for, the underlying layers. In order to address this discrepancy for calibration purposes, sheet resistance measurements for both 4-pt top film, as well as substrate, are used in some examples to calculate the equivalent parallel net resistance which is then used to calibrate the applicable eddy sensor.

Figure 4:
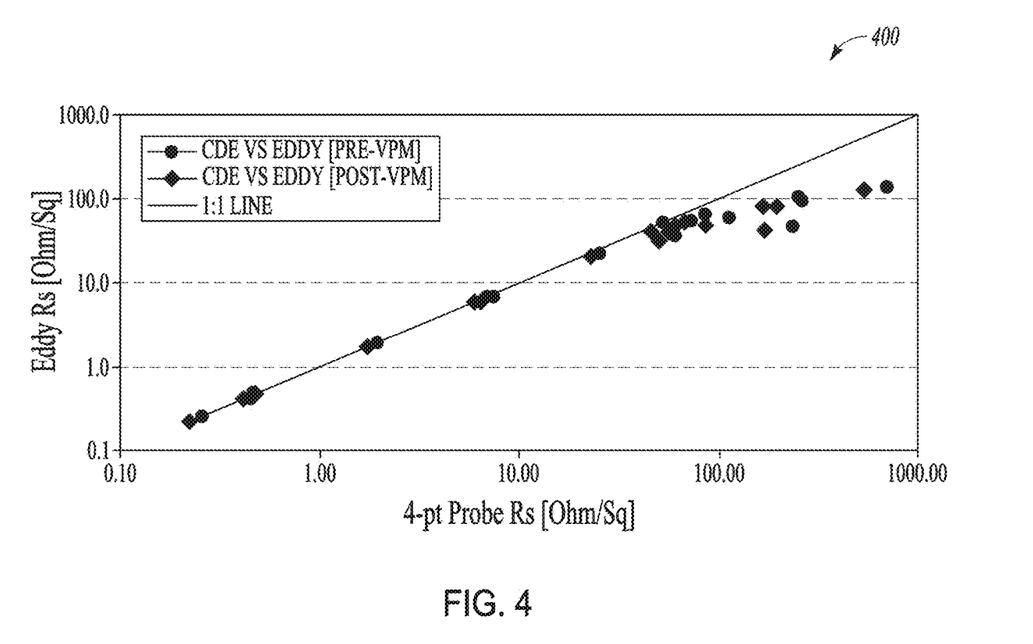
FIG. 4 includes a graph depicting sheet resistance values, according to example embodiments.

FIG. 4 includes a graph 400 illustrating sheet resistance (Rs) values of seed layers on test substrates obtained respectively by example eddy-based methods described herein and conventional 4-pt probe methods. As shown, there is a strong correlation between the two for both pre and post treatment in a VPM. The absolute Rs values are comparable between a 4-pt probe and an eddy sensor up to approximately 50 ohm/sq. Eddy sensor measurements are lower at higher Rs due to a larger proportion of underlying layer contribution in a net Rs measurement. The percentage Rs drop trend is also comparable between a 4-pt probe and eddy sensor. The percentage Rs drop may be slightly higher for lower sheet resistance measurements due to an inherent measurement delay during 4-pt probe measurements. An Rs drop seen in the eddy sensor results may be lower at higher seed layer sheet resistance value because the absolute Rs is lower due to the presence of underlying layers of the seed layer.

Some examples of the present disclosure include calibration substrates. In an example, a configured set of titanium (Ti), titanium nitride (TiN), and aluminum (Al) films were deposited by PVD process on a high sheet resistance silicon substrate to create a set of calibration substrates having a known range of sheet resistance. In some examples, low or no doping was used such that the sheet resistance of the substrate on the calibration substrate is much more than the highest range of the expected sheet resistance of a target substrate, such that influence of the underlying layer is much smaller compared to the top layer. Moreover, it is possible in some examples to use the same metal in a calibration film set to establish a range of sheet resistance by varying the metal thickness; however, here it was seen that the on-substrate non-uniformity in the thickness across the substrate was higher with thinner film and lower with relatively thicker films. For this reason, a set of metal films, such as those discussed above, was used to seek to ensure that the uniformity is similar across the range of calibration substrates. Ti and TiN have higher sheet resistance and may be used for calibration substrates in the higher end of a sheet resistance range, while Al has a relatively lower sheet resistance so a thicker film could be used to achieve a lower calibrated sheet resistance with better uniformity across the substrates. Ti and TiN are resistant to oxidation and have stable oxide while Al may be more suitable in relatively lower sheet resistance ranges in applications having thicker films and where oxidation causes a small change only in the overall sheet resistance.

Figure 5:
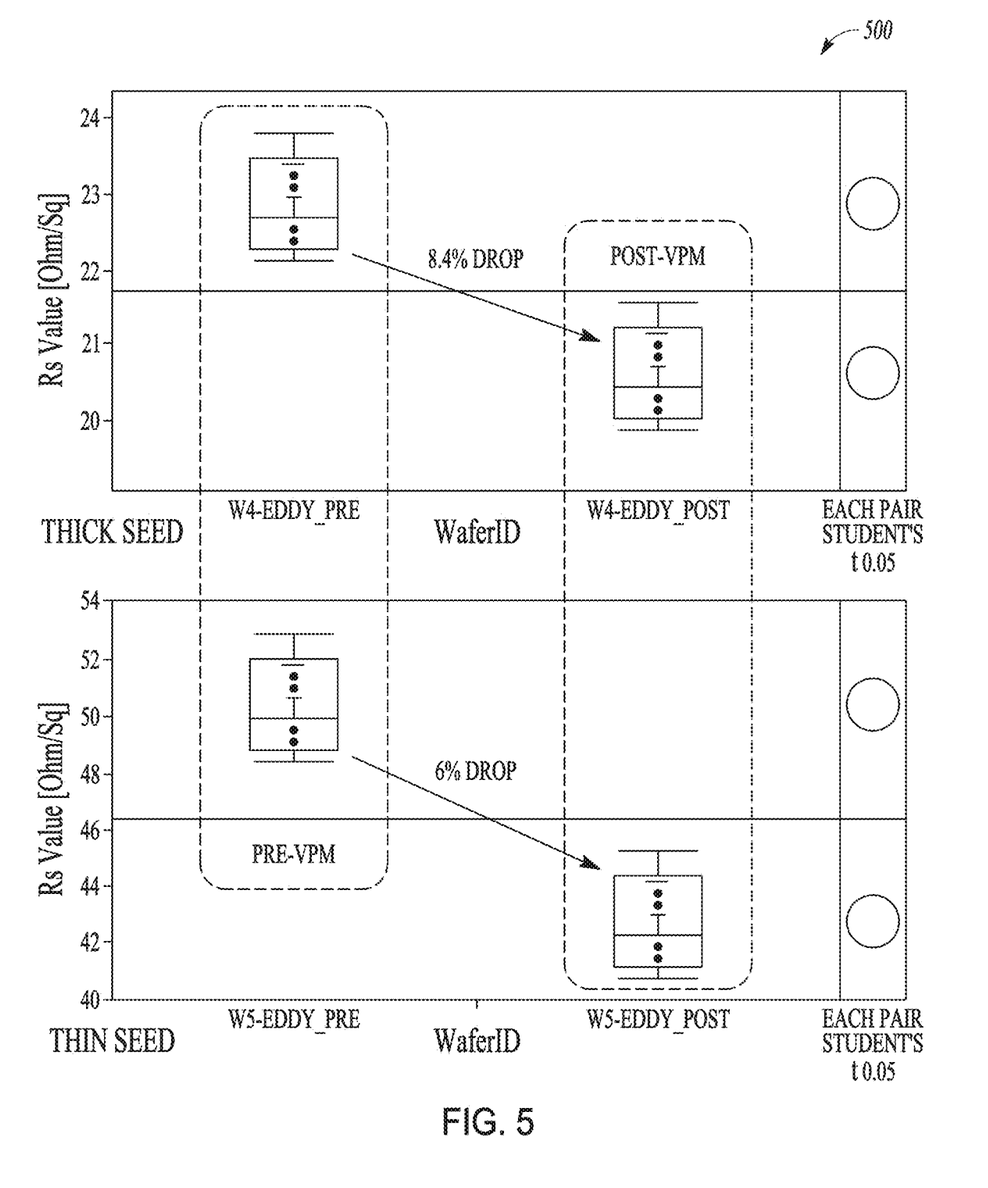
FIG. 5 includes a table and graphs illustrating results obtained from testing performed on an example VPM metrology system, according to example embodiments.

FIG. 5 includes a table and graphs 500 illustrating results obtained from testing performed on an example VPM metrology system in relation to calibration stability, defect performance, and measurement repeatability. Thin seed and thick seed substrates were tested. The system performed acceptably on all aspects. A statistically significant, repeatable, and stable decrease in sheet resistance (Rs) value is observed in the two representative test cases presented here for thicker and thinner seed. This precise and stable change in sheet resistance value before and after VPM treatment indicates that this device and calibration method can be used as an in-line verification of VPM treatment efficacy for each substrate that is processed. Rs drops were consistently measured with the present VPM metrology and the changes measured were statistically significant compared to the range of data in the individual box plots.

In other aspects, some examples may include enhancements to the robot of a VPM. For example, robot firmware can be implemented to include specially configured robot stations to enable accurate, repetitive, and consistent calibration and ensure that the same measurement position on each measured substrate was addressed during calibration to minimize variability caused by sheet resistance non-uniformity on the calibration samples. This may be significant for two-sensor configurations in which sensor-to-sensor matching can be important. Sensor matching may be achieved in some examples by ensuring that both sensors are calibrated with precisely the same sample at precisely the same measurement position to reduce calibration variability.

Other example robot firmware enhancements may include specific methods for handling automated calibration in the field to reduce maintenance and downtime on the tool processing substrates being measured by the VPM metrology system. In some examples, automated calibration includes a functionality for the sensor to communicate with associated software, which in turn can communicate with robot handlers to process detailed calibration using a range of specific calibration substrates having known sheet resistance values.

In some examples, an automated calibration method includes, by a sensor controller, differentiating between a calibration substrate and measurement substrate (i.e., a substrate to be measured). For the calibration substrate, the sensor controller automatically generates a calibration curve based on a measurement of a range of calibration substrates. In an effort to avoid or minimize errors occurring during a calibration substrate run, some failsafe methods may include updating partially calibrated curves, or rejecting suspicious (or out of bounds) calibrated points and reverting to a known good calibration curve. Specific details may be built into the associated software to quantify the quality of the calibration curve. The sensor controller may include functionality to provide a status of the measurement and associated errors.

Some example methods include providing a specific response to the sensor controller in the case of a hardware setup issue (for example, including a measurement out of range, a noise in a signal, a temperature related instability, a vibration, or accidental mismatch in a mounting setup). Specific routines may be established to perform automated self-reference, comparison of self-reference with good known values, auto-calibration, and the generation of a request for manual calibration in extreme cases of a detected issue. Frequent self-reference of a signal in air with no substrate sample has also been implemented, which was found to help with the signal drift quite a bit.

Some examples include external measurement noise processing techniques to post-process measurement data. There is typically some inherent noise associated with millisecond level eddy sensor data collection that may be caused by multi-sensor electronic noise and interference with outside electromagnetic noise. Here, shielding and good grounding can be helpful. Power supply related fluctuations and high frequency vibration on the tool may also contribute to some of the measurement noise of the eddy sensors. Multiple grounding and shielding boxes are used in some examples to achieve stable measurements. A post processing routine may include a User Datagram Protocol (UDP) based communication protocol that samples high frequency data and generates a line-scan that may include a specific number of points on the substrate during measurement. This technique may be implemented to address or remove high frequency noise. A specific representative measurement may be acquired at a pre-determined point on the substrate.

Figure 6:
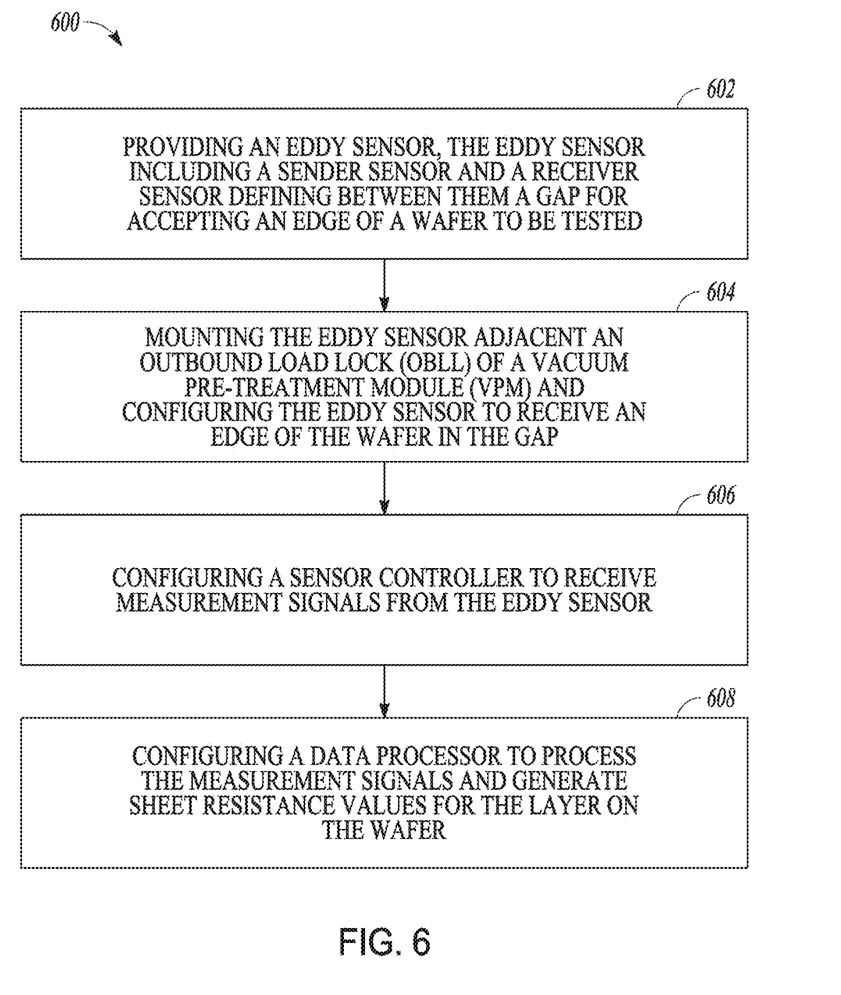
FIG. 6 is a flow chart illustrating operations in a method, according to example embodiments.

Some examples of the present disclosure include methods. With reference to FIG. 6, a method 600 of measuring a sheet resistance of a layer on a substrate is provided. The method 600 may comprise: at 602, providing an eddy sensor, the eddy sensor including a sender sensor and a receiver sensor defining between them a gap for accepting an edge of a substrate to be tested; at 604, mounting the eddy sensor adjacent an outbound load lock (OBLL) of a vacuum pre-treatment module (VPM) and configuring the eddy sensor to receive an edge of the substrate in the gap; at 606, configuring a sensor controller to receive measurement signals from the eddy sensor; and, at 608, configuring a data processor to process the measurement signals and generate sheet resistance values for the layer on the substrate.

In some examples, the method 600 further comprises configuring a trigger sensor to detect a threshold proximity of the substrate and generate a signal to initiate activation of the sender and receiver sensors.

In some examples, the method 600 further comprises setting the gap size in the range 3-10 mm.

In some examples, the method 600 further comprises setting the gap size at 5 mm.

In some examples, the method 600 further comprises configuring the eddy sensor to take a measurement at a measurement position on the substrate, wherein the measurement position is disposed at a location midway between a center of the substrate and an edge of the substrate.

In some examples, the method 600 further comprises configuring the system to measure sheet resistance for a copper (Cu) seed substrate in the range of approximately 0.001 to 30 ohms-per-square (ohm/sq).

In some examples, the method 600 further comprises configuring the system to measure sheet resistance for a cobalt (Co) seed substrate in the range of approximately 1 ohm/sq to 10,000 ohm/sq.

In some examples, the method 600 further comprises configuring the system to measure sheet resistance up to 50.000 ohm/sq.

In some examples, the method 600 further comprises configuring the eddy sensor to accept substrates in-situ for sheet resistance measurements during a production run of the VPM.

In some examples, a straight-line path of a substrate exiting the OBLL for a sheet resistance measurement is coincident with an in-line scan path of the eddy sensor.

Figure 7:
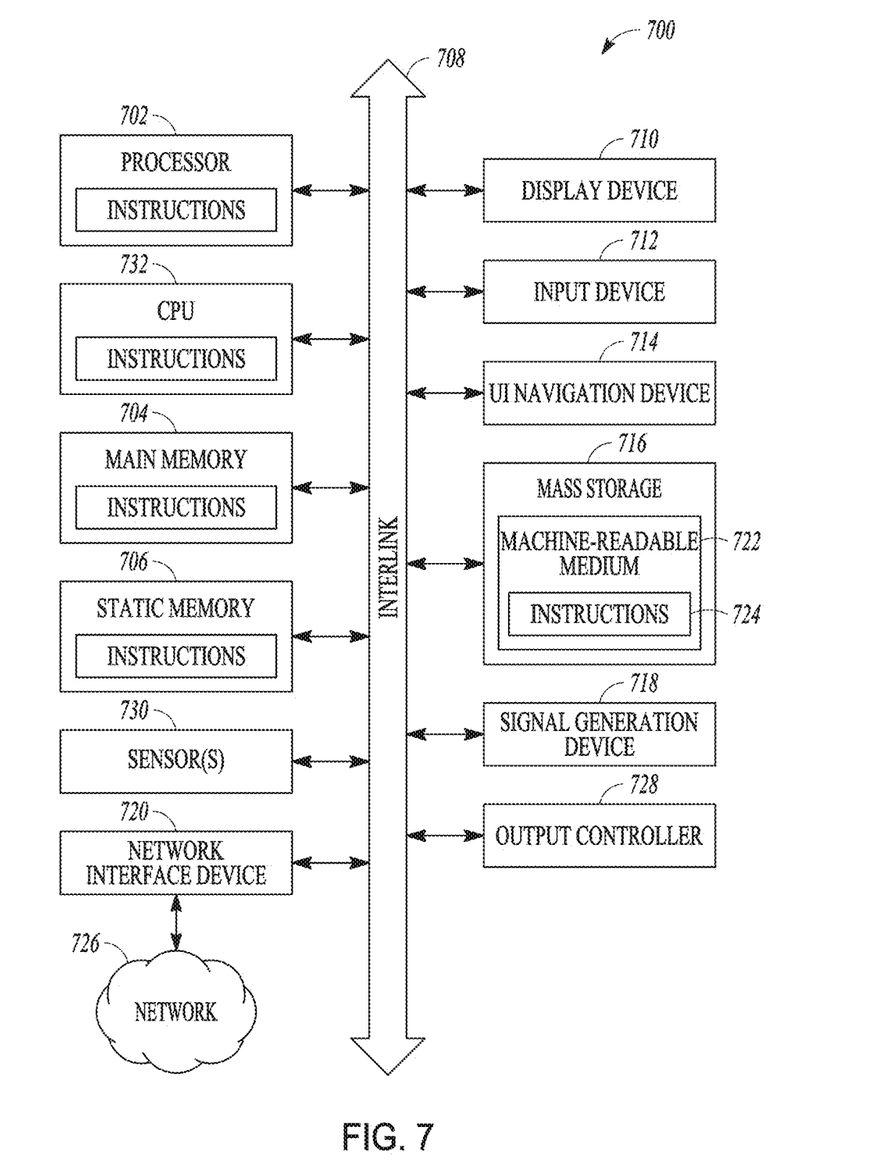
FIG. 7 is a block diagram illustrating an example of a machine upon which one or more example embodiments may be implemented, or by which one or more example embodiments may be controlled.

FIG. 7 is a block diagram illustrating an example of a machine or controller 700 by which one or more example embodiments described herein may be controlled. In alternative embodiments, the controller 700 may operate as a standalone device or may be connected (e.g., networked) to other machines. In a networked deployment, the controller 700 may operate in the capacity of a server machine, a client machine, or both in server-client network environments. In an example, the controller 700 may act as a peer machine in a peer-to-peer (P2P) (or other distributed) network environment. Further, while only a single controller 700 is illustrated, the term "machine" (controller) shall also be taken to include any collection of machines (controllers) that individually or jointly execute a set (or multiple sets) of instructions to perform any one or more of the methodologies discussed herein, such as via cloud computing, software as a service (SaaS), or other computer cluster configurations. In some examples, and referring to FIG. 7, a non-transitory machine-readable medium includes instructions 724 that, when read by a controller 700, cause the controller to control operations in methods comprising at least the non-limiting example operations described herein.

Examples, as described herein, may include, or may operate by logic, a number of components, or mechanisms. Circuitry is a collection of circuits implemented in tangible entities that include hardware (e.g., simple circuits, gates, logic, etc.). Circuitry membership may be flexible over time and underlying hardware variability. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a computer-readable medium physically modified (e.g., magnetically, electrically, by moveable placement of invariant massed particles, etc.) to encode instructions of the specific operation. In connecting the physical components, the underlying electrical properties of a hardware constituent are changed (for example, from an insulator to a conductor or vice versa). The instructions enable embedded hardware (e.g., the execution units or a loading mechanism) to create members of the circuitry in hardware via the variable connections to carry out portions of the specific operation when in operation. Accordingly, the computer-readable medium is communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry, at a different time.

The machine (e.g., computer system) 700 may include a hardware processor 702 (e.g., a central processing unit (CPU), a hardware processor core, or any combination thereof), a graphics processing unit (GPU) 732, a main memory 704, and a static memory 706, some or all of which may communicate with each other via an interlink (e.g., bus) 708. The controller 700 may further include a display device 710, an alphanumeric input device 712 (e.g., a keyboard), and a user interface (UI) navigation device 714 (e.g., a mouse). In an example, the display device 710, alphanumeric input device 712, and UI navigation device 714 may be a touch screen display. The controller 700 may additionally include a mass storage device (e.g., drive unit) 716, a signal generation device 718 (e.g., a speaker), a network interface device 720, and one or more sensors 730, such as a Global Positioning System (GPS) sensor, compass, accelerometer, or another sensor. The controller 700 may include an output controller 728, such as a serial (e.g., universal serial bus (USB)), parallel, or other wired or wireless (e.g., infrared (IR), near field communication (NFC), etc.) connection to communicate with or control one or more peripheral devices (e.g., a printer, card reader, etc.).

The mass storage device 716 may include a machine-readable medium 722 on which is stored one or more sets of data structures or instructions 724 (e.g., software) embodying or utilized by any one or more of the techniques or functions described herein. The instructions 724 may as shown also reside, completely or at least partially, within the main memory 704, within the static memory 706, within the hardware processor 702, or within the GPU 732 during execution thereof by the controller 700. In an example, one or any combination of the hardware processor 702, the GPU 732, the main memory 704, the static memory 706, or the mass storage device 716 may constitute machine-readable media 722.

While the machine-readable medium 722 is illustrated as a single medium, the term "machine-readable medium" may include a single medium, or multiple media (e.g., a centralized or distributed database, and/or associated caches and servers) configured to store the one or more instructions 724.

The term "machine-readable medium" may include any medium that can store, encode, or carry instructions 724 for execution by the controller 700 and that cause the controller 700 to perform any one or more of the techniques of the present disclosure, or that can store, encode, or carry data structures used by or associated with such instructions 724. Non-limiting machine-readable medium examples may include solid-state memories, and optical and magnetic media. In an example, a massed machine-readable medium comprises a machine-readable medium 722 with a plurality of particles having invariant (e.g., rest) mass. Accordingly, massed machine-readable media are not transitory propagating signals. Specific examples of massed machine-readable media may include non-volatile memory, such as semiconductor memory devices (e.g., electrically programmable read-only memory (EPROM), electrically erasable programmable read-only memory (EEPROM)) and flash memory devices; magnetic disks, such as internal hard disks and removable disks; magneto-optical disks; and CD-ROM and DVD-ROM disks. The instructions 724 may further be transmitted or received over a communications network 726 using a transmission medium via the network interface device 720.

Although examples have been described with reference to specific example embodiments or methods, it will be evident that various modifications and changes may be made to these embodiments without departing from the broader scope of the embodiments. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This detailed description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A Vacuum Pre-treatment Module (VPM) metrology system for measuring a sheet resistance of a layer on a substrate, the system comprising:
   an eddy sensor, the eddy sensor including a first magnetic coupling sensor and a second magnetic coupling sensor defining a gap between them for accepting an edge of the substrate in the gap, the eddy sensor positioned adjacent an outbound load lock (OBLL) of the VPM;
   a sensor controller to receive measurement signals from the first and second magnetic coupling sensors;
   a data processor to process the measurement signals and generate a sheet resistance value for the layer on the substrate, and
   a trigger sensor to generate a signal to initiate a sheet resistance measurement action based on a detected passage of the substrate exiting the OBLL of the VPM.

2. The system of claim 1, wherein a size of the gap is in a range 3-50 mm.

3. The system of claim 2, wherein the gap size is 5 mm.

4. The system of claim 1, wherein the eddy sensor is configured to take a measurement at a measurement position on the substrate, wherein the measurement position is disposed at a location midway between a center of the substrate and an edge of the substrate.

5. The system of claim 1, wherein the layer includes a copper (Cu) seed substrate and wherein the generated sheet resistance value is in a range of approximately 0.001 to 30 ohms-per-square (ohm/sq).

6. The system of claim 1, wherein the layer includes a cobalt (Co) seed substrate and wherein the generated sheet resistance value is in a range of approximately 1 ohm/sq to 10,000 ohm/sq.

7. The system of claim 1, wherein the system is configured to measure sheet resistance up to 50,000 ohm/sq.

8. The system of claim 1, wherein the eddy sensor is disposed immediately adjacent an outbound load lock (OBLL) of the VPM and is configured to accept substrates in-situ for sheet resistance measurements during a production run of the VPM.

9. The system of claim 8, wherein a straight-line path of the substrate exiting the OBLL for a sheet resistance measurement is coincident with an in-line scan path of the eddy sensor.

10. A method, by a Vacuum Pre-treatment Module (VPM) metrology system, for measuring a sheet resistance of a layer on a substrate, the method comprising:
    providing an eddy sensor, the eddy sensor including a first magnetic coupling sensor and a second magnetic coupling sensor defining between them a gap for accepting an edge of the substrate in the gap;
    mounting the eddy sensor adjacent an outbound load lock (OBLL) of a vacuum pre-treatment module (VPM) and configuring the eddy sensor to receive an edge of the substrate in the gap;
    configuring a sensor controller to receive measurement signals from the eddy sensor;
    configuring a data processor to process the measurement signals and generate a sheet resistance value for the layer on the substrate, and
    configuring a trigger sensor to generate a signal to initiate a sheet resistance measurement action based on a detected passage of the substrate exiting the OBLL of the VPM.

11. The method of claim 10, further comprising setting a gap size in a range 3-10 mm.

12. The method of claim 11, further comprising setting the gap size at 5 mm.

13. The method of claim 10, further comprising configuring the eddy sensor to take a measurement at a measurement position on the substrate, wherein the measurement position is disposed at a location midway between a center of the substrate and an edge of the substrate.

14. The method of claim 10, wherein the layer includes a copper (Cu) seed substrate and wherein the method further comprises generating the sheet resistance value in a range of approximately 0.001 to 30 ohms-per-square (ohm/sq).

15. The method of claim 10, wherein the layer includes a cobalt (Co) seed substrate and wherein the method further comprises generating the sheet resistance value in a range of approximately 1 ohm/sq to 10,000 ohm/sq.

16. The method of claim 10, further comprising configuring the VPM metrology system to measure sheet resistance up to 50,000 ohm/sq.

17. The method of claim 10, further comprising configuring the eddy sensor to accept substrates in-situ for sheet resistance measurements during a production run of the VPM.

18. The method of claim 17, wherein a straight-line path of the substrate exiting the OBLL for a sheet resistance measurement is coincident with an in-line scan path of the eddy sensor.

19. A non-transitory computer readable storage medium comprising instructions stored therein for causing a computer processor to execute a method for measuring a sheet resistance of a layer on a substrate, the method comprising:
- accessing an eddy sensor, the eddy sensor including a first magnetic coupling sensor and a second magnetic coupling sensor defining between them a gap for accepting an edge of the substrate, the eddy sensor positioned adjacent an outbound load lock (OBLL) of a vacuum pre-treatment module (VPM) and configured to receive the edge of the substrate in the gap;
- accessing a sensor controller configured to receive measurement signals from the eddy sensor;
- accessing a data processor configured to process the measurement signals and generate a sheet resistance value for the layer on the substrate; and
- accessing a trigger sensor to generate a signal to initiate a sheet resistance measurement action based on a detected passage of the substrate exiting the OBLL of the VPM.

* * * * *